United States Patent [19]

Thomas

[11] Patent Number: 5,010,564
[45] Date of Patent: Apr. 23, 1991

[54] DUAL AXIS TRANSLATION MECHANISM

[75] Inventor: Howard C. Thomas, Westminster, Colo.

[73] Assignee: Eureka X-Ray Tube, Inc., Chicago, Ill.

[21] Appl. No.: 406,991

[22] Filed: Sep. 14, 1989

[51] Int. Cl.⁵ .......................................... G03B 42/04
[52] U.S. Cl. .................... 378/176; 378/181; 269/71
[58] Field of Search ...................... 378/175, 176, 181; 269/55, 58, 59, 71

[56] References Cited

U.S. PATENT DOCUMENTS

| | | | |
|---|---|---|---|
| 3,355,730 | 11/1967 | Neasham | 340/286 |
| 3,383,506 | 5/1968 | Bock et al. | 250/66 |
| 3,555,276 | 1/1971 | Endesfelder et al. | 378/176 |
| 3,848,134 | 11/1974 | Gieschen et al. | 250/471 |
| 4,071,767 | 1/1978 | Pury et al. | 378/176 |
| 4,105,920 | 8/1978 | Pury et al. | 250/402 |
| 4,412,383 | 11/1983 | Landa | 33/1 M |
| 4,417,357 | 11/1983 | Le Sonn | 378/176 |
| 4,420,886 | 12/1983 | Amano | 33/1 M |
| 4,489,428 | 12/1984 | Schwieker | 378/176 |
| 4,559,641 | 12/1985 | Caugant et al. | 378/181 |
| 4,577,341 | 3/1986 | Schwieker et al. | 378/150 |
| 4,845,734 | 7/1989 | Maki et al. | 378/181 |

FOREIGN PATENT DOCUMENTS 1948037 3/1971 Fed. Rep. of Germany .
323655 9/1957 Switzerland .

Primary Examiner—Carolyn E. Fields
Assistant Examiner—David P. Porta
Attorney, Agent, or Firm—Lawrence C. Edelman

[57] ABSTRACT

A mechanism for selective translation of an object along first and second axes comprises a frame, a carriage mounted on the frame for sliding movement with respect to the frame along the first axis, a holder for said object and an intermediate mounting means coupled to the holder and the carriage for mounting the holder on the carriage for sliding movement with respect to the carriage along the second axis. A motor is provided for selectively driving a first shaft and a drive/brake assembly provides a second shaft. In a drive mode of the assembly the second shaft is allowed to be driven synchronously with the first shaft and, in a brake mode of the assembly, is held non-driven while the first shaft is being driven. First and second endless belts are coupled to the first and second shafts, respectively, for receiving selective rotational movement therefrom. The first belt is also coupled to the intermediate mounting means for causing selective movement of the object holder along the second axis and the second belt is also coupled with the carriage for causing selective movement of the carriage along the first axis. In operation, when both belts are rotated, the second belt causes the carriage to move along the second axis, while the intermediate mounting means does not cause movement of the object holder due to the synchronous movement of the intermediate mounting means with the first belt due to coupling of the intermediate mounting means on the carriage. However, when the second belt is not driven during the brake mode of the drive/brake assembly, relative movement of said first belt with said intermediate mounting means causes sliding movement of the object holder along the second axis.

25 Claims, 5 Drawing Sheets

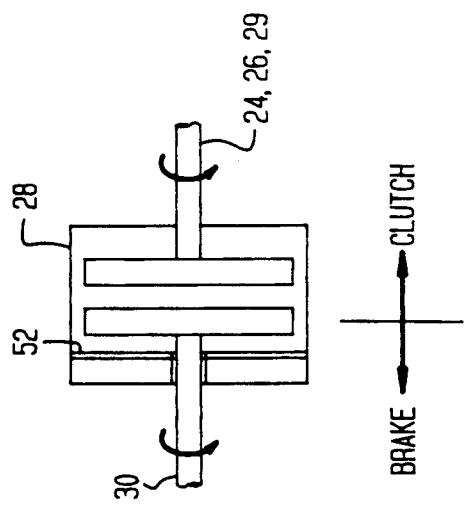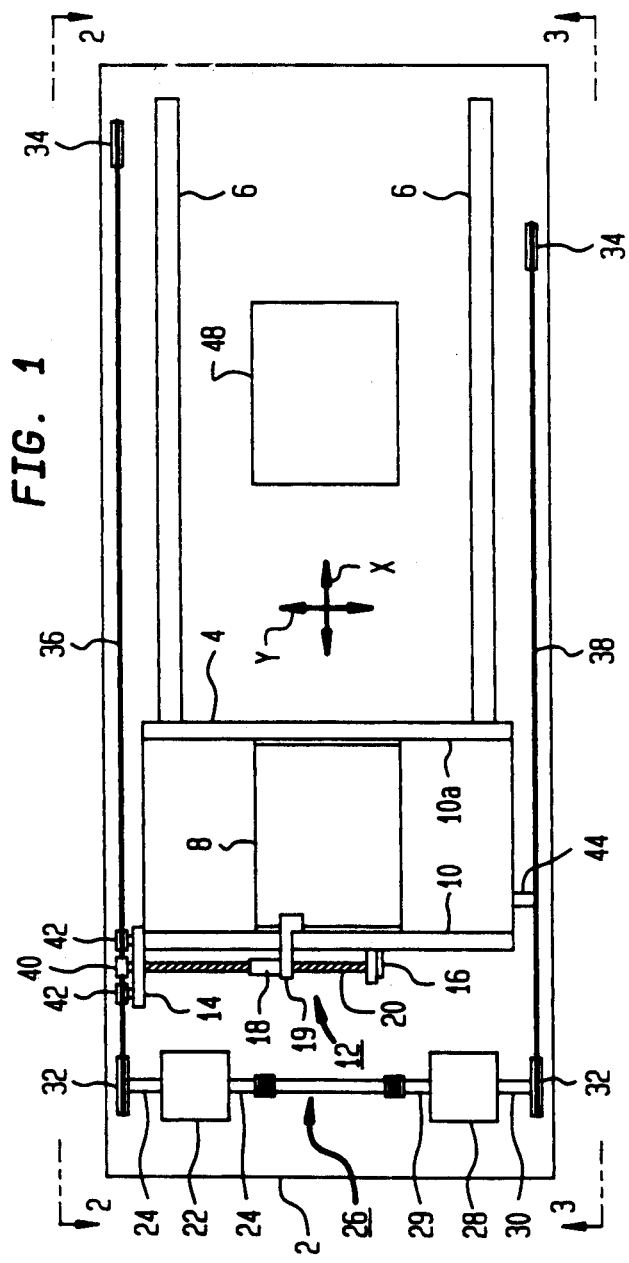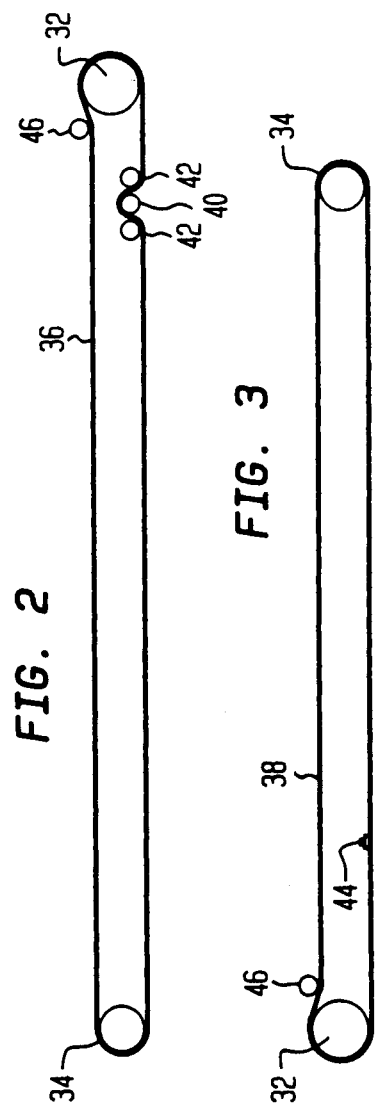

DUAL AXIS TRANSLATION MECHANISM

BACKGROUND OF THE INVENTION

1. Field of the Invention

This invention relates generally to an improved dual axis translation mechanism and in particular to an x-y translation mechanism useful in an x-ray spot film device 2. Description of the Prior Art Conventional spot film devices usually comprise a support or frame extending crosswise over the top of an x-ray table. A main carriage is mounted on the support for being advanced from a rearward parked position to a frontward radiographic position wherein a film cassette carried by the carriage is disposed in alignment with an x-ray beam that is projected through a patient from an x-ray source in the table. The film cassette is mounted in a tray supported on an inner carriage which is translatable with respect to the main carriage so that the center of the collimated x-ray beam may be made coincident with an area on the film cassette where one or a sequence of spot film exposures are to be made. The area is further defined by superimposable x-ray masks.

As is well known, spot film devices are also used in conjunction with a fluoroscopic device which permits an examining radiologist to visualize anatomy of interest before making one or more radiographs in a choice of sizes by translating the film cassette forward and shifting it, and the masks, to obtain the desired sequence of radiographs. The fluoroscopic device on the spot film device is aligned with the x-ray source in the table, and the film cassette is, of course, retracted from the x-ray beam during fluoroscopy.

When a fluoroscopic view of interest is observed, the film cassette must be projected into the x-ray beam path rapidly and one or more exposures must be taken while the fluoroscopically observed condition persists.

The x-y translating mechanism of spot film devices generally employ electromechanical means for rapidly advancing and retracting the film cassette between load and parked positions and between parked and the various positions in which the sequence of radiographs are taken. In addition, means are provided for predetermining the sequence and for cushioning the shock forces that are incidental to rapid transfer of the film cassette carriage from the parked position to its other positions when alternating between fluoroscopic and radiographic or loading modes.

These functions have been achieved in known translation mechanisms by complicated arrangements of mechanical linkages, tracks, cams, relays, belts and so forth, which accomplished their purposes under manual or mechanical influence or under a combination of such influences. Cassette translation mechanisms including motor drive means typically include two reversable motors, one motor for each of the orthogonal directions in which the film cassette must be driven. The requirement of two motors undesirably increases the weight and power consumption of the drive system. In other types of motor systems having one and/or two motors, as a motor moves the film cassette rearwardly to a parked position, it slowly loads a return spring at the same time. The film carriage is latched in the parked position and when the latch is released, the carriage is advanced rapidly under the influence of the spring and halted abruptly in the radiographic position. Rapid movement and abrupt halt of the film carriage results in considerable noise, shock and vibration that necessitates use of shock absorbing devices such as dash pots to reduce these ill effects. One problem with this type of system is that the main carriage must be restored to a rearward position after each exposure, to reload the spring, after which the carriage must be projected forwardly again to make the next exposure.

Other types of prior spot film devices have a set of tracks for the main carriage After each exposure, the carriage is returned rearwardly and shifted to different tracks, similar to railroad car switching. When the carriage is driven forwardly, it arrives in the proper position for the next exposure to be made. This is a relatively slow method and requires a large and complicated mechanism which has many moving parts.

The above arrangements have resulted in lower than desirable reliability, increased power consumption, a massiveness that has had to be off-set with increased counterweight and/or power and a noisy operation. Some of the complexity and size resulted from spot devices being adapted to accommodate rectangular cassettes in their long and short dimensions in which case means had to be provided for altering the mode of operation of the transfer and sequence mechanism depending on how the cassette was oriented in its holder.

The present invention is directed to overcoming the abovenoted disadvantages. It is a general object of this invention to provide a translation mechanism particularly useful in a spot film device that is simple in construction, lightweight, operates quietly, efficiently, safely, and automatically, is simple to operate and maintain and is comparatively inexpensive to manufacture.

SUMMARY OF THE INVENTION

A mechanism for selective translation of an object along first and second axes, comprises a frame, a carriage mounted on the frame for movement with respect to the frame along a first axis, a holder for said object and an intermediate mounting means coupled to the holder and the carriage for mounting the holder on the carriage for movement with respect to the carriage along a second axis which is different from the first axis. A motor is provided for selectively driving a first shaft. A drive/brake assembly provides a second shaft which, in a drive mode of the assembly is caused to be driven synchronously with the first shaft and, which in a brake mode of the assembly, is held nondriven while the first shaft is being driven. First and second endless belts are mounted for rotating movement within the frame and extend along the first axis. The first and second belts are coupled to the first and second shafts, respectively, for selectively receiving rotational movement therefrom. The first belt is also coupled to the intermediate mounting means so as to drive a portion thereof for causing selective movement of the object holder along the second axis and the second belt is coupled with the carriage for causing selective movement of said carriage along the first axis. In operation, when both belts are synchronously rotated, the second belt causes the carriage to move along the first axis, while the intermediate mounting means does not cause movement of the object holder because of the synchronous movement of the intermediate mounting means with the first belt due to coupling of the intermediate mounting means on the carriage. However, when the second belt is not driven during the brake mode of the drive/brake assembly, relative movement of said first belt with said intermediate mounting means causes movement of the object holder along the second axis.

Controlled movement of the first and second shafts by the motor and drive/brake assembly results in the ability to rapidly position the object holder at any desired position along the first and second axes in a simple, efficient and reliable manner. Other features and advantages of the invention will be apparent from the description of the preferred embodiment and from the claims.

In a preferred embodiment of the invention, the drive/brake assembly comprises a clutch/brake assembly having an input shaft which is driven by the same motor which drives the first shaft.

For a fuller understanding of the present invention, reference should now be made to the following detailed description of the preferred embodiment of the invention and to the accompanying drawings.

BRIEF DESCRIPTION OF THE DRAWINGS

FIG. 1 illustrates a dual axis translating mechanism constructed in accordance with the principles of the invention;

FIGS. 2 and 3 illustrate details of the first and second drive belts illustrated in FIG. 1;

FIG. 4 illustrates in simplified form the clutch/brake assembly shown in FIG. 1;

DETAILED DESCRIPTION OF THE PREFERRED EMBODIMENTS

Figure 5:
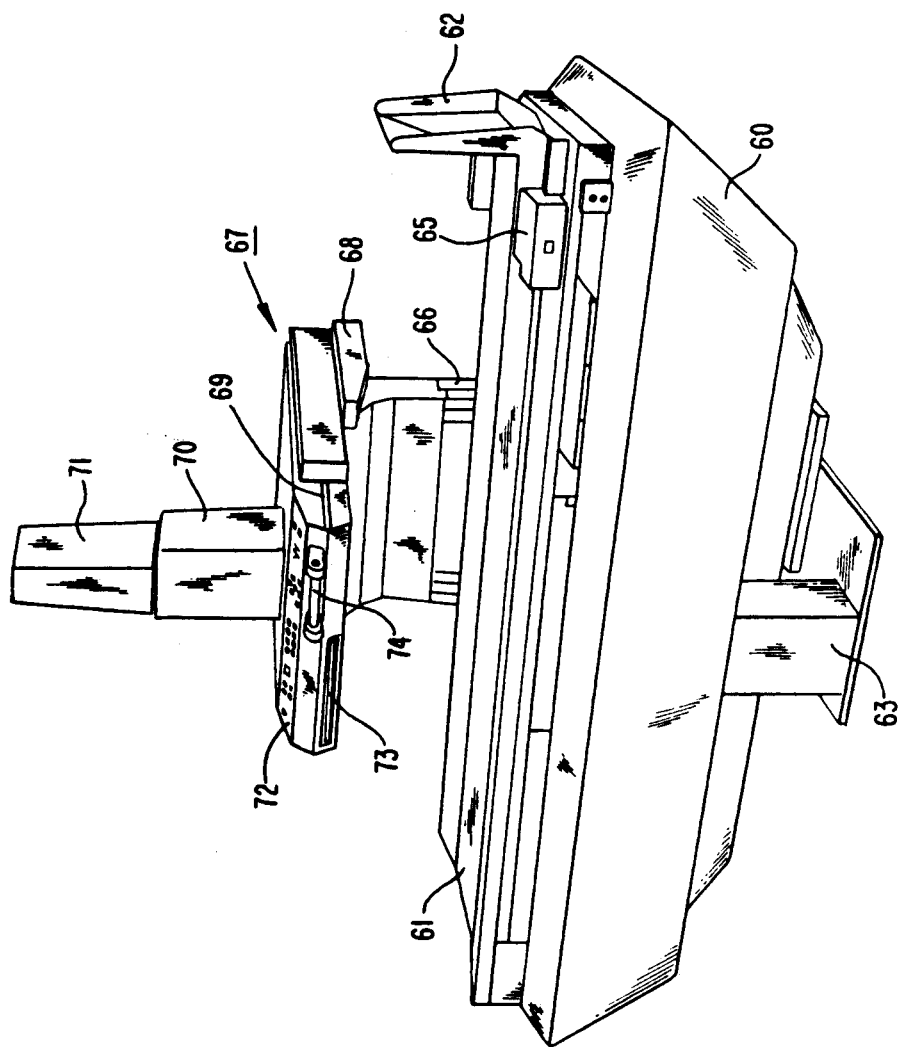
FIG. 5 illustrates a diagnostic x-ray table including a spot film device.

FIG. 1 shows a top view of the mechanical portions of the dual axis translating mechanism, arranged for use in a spot film device. The electrical portions of the arrangement are not shown since they are of conventional design for a spot film device, with some slight variations (e.g., for controlling the clutch/brake mechanism, to be described) which would be obvious to those of ordinary skill in the art. A frame 2 includes a carriage 4 which is mounted within the frame for sliding movement along a first axis, indicated by arrow X, via guide means 6. Guide means 6 preferably comprises a set of parallel-spaced ball-bearing linear slides, in order to allow smooth rapid movement of carriage 4 along the x-axis.

An object holder 8 is mounted on carriage 4 for sliding movement along a second axis, indicated by arrow Y, via an intermediate mounting means including a guide means 10, 10a and a lead-screw assembly 12. Guide means 10, 10a may also comprise a set of parallel-spaced ball-bearing linear slides, or, for cost reduction, a nylon bar may be substituted for guide means 10a, for slidingly supporting an edge of object holder 8. Lead-screw assembly 12 is mounted to carriage 4 via brackets 14 and 16 and includes a rotatable lead-screw 20 having a following nut 18 which is coupled to object holder 8 via a bracket 19. Rotation of lead screw 20 causes linear movement of nut 18, and thus object holder 8, in the y-axis direction.

A motor 22 is provided for selectively driving a first shaft 24. One end of shaft 24 is coupled, via a flexible coupling 26, to a clutch/brake assembly 28 for selectively driving a second shaft 29, 30. As well known, when assembly 28 is in its clutch mode of operation, its drive shafts 29 and 30 rotate synchronously, while in its brake mode of operation, drive shaft 29 (and hence shaft 24) is allowed to rotate while shaft 30 is held so as to not rotate. Details of clutch/brake assembly 28 are shown in FIG. 4 and described later on. Shafts 24 and 30 each include a drive pulley 32 at their ends and frame 2 includes corresponding idler pulleys 34 for supporting first and second endless belts 36 and 38, respectively, so that the belts extend within frame 2 along the x-axis direction. Drive pulleys 32 preferably have the same outside diameter for causing the first and second belts to be driven at the same linear speed when said first and second shafts are simultaneously driven. Belt 36 is coupled to lead-screw assembly 12 via pressure of belt 36 against a drive pulley 40 attached to one end of lead-screw 20. The pressure is exerted via idler pulleys 42 which are rotatably attached to bracket 14. Idler pulleys 42 are adjusted to provide more than 100° of wrap about drive pulley 40. Belt 38 is connected to carriage 4 via a clamp type of connecting means 44. FIGS. 2 and 3 show side views of the above-described details of the connection of belts 36 and 38, and additionally show the use of further idler pulleys 46 mounted within frame 2 for maintaining proper tension in belts 36 and 38. When the above-described arrangement is used in a spot film device for holding a film cassette and controlling its position, frame 2 would include a port 48 therein through which the x-rays which pass through the patient are allowed to impinge upon the film within holder 8.

The operation of the above-described arrangement is as follows. For movement of object holder 8 in the x-axis direction, motor 22 is energized for rotation of shaft 24 in the desired direction for an appropriate time period while clutch/brake assembly is caused to be in its clutch mode. As shafts 24, 29 and 30 rotate, belts 36 and 38 rotate at the same speed, with belt 38 causing movement of carriage 4 in the x-axis direction. Since lead-screw assembly 12 is mounted upon carriage 4, it also moves in the x-axis direction, thereby resulting in no relative movement between lead-screw assembly 12 and belt 36. Thus, when clutch/brake assembly 28 is in the clutch mode, appropriate energization of motor 22 controls the speed and sense of movement of object holder 8 in the x-axis direction. However, when clutch/brake assembly 28 is in the brake mode, shaft 30 is held non-rotating, while shafts 29, 24 rotate. Thus, belt 38 is held non-rotating, preventing movement of carriage 4, while belt 36 is rotated, thereby driving pulley 40 of lead-screw assembly 12 and causing movement of object holder 8 in the y-axis direction. Consequently, appropriate energization of motor 22 and clutch/brake assembly 28 allows complete control for positioning object holder 8 anywhere within the x-y coordinate axis system.

FIG. 4 illustrates in simplified form, details of the clutch/brake assembly 28 shown in FIG. 1. The opposing ends of shafts 30 and 24, 26 are enlarged and coated with a suitable material (or include an appropriate apparatus therebetween) so that when shaft 30 is urged to the right (as shown in FIG. 4) by an electromechanical shifting means (not shown) of known design, both shafts will be coupled so as to rotate in synchronism, resulting in the clutch mode of operation of assembly 28. However, when shaft 30 is urged to the left, its enlarged end is forced into contact with an abrasive material 52, resulting in rapid deceleration and non-rotation of shaft 30, while shafts 24, 29 are allowed to continue to rotate, resulting in the brake mode of operation.

FIG. 5 is a perspective view of a typical diagnostic x-ray table incorporating a spot film device improved in accordance with the present invention. The table comprises a body 60 in which there is an x-ray source, not shown. When energized, the x-ray source projects a collimated x-ray beam through table top 61 on which a patient undergoing x-ray examination may be reposed. The top has a foot rest 62 for supporting the patient in an upright position when the table body 60 is tilted clockwise from the position in which it is shown. Table body 60 is supported from a floor stand 63 with respect to which body 60 may be tilted and translated to clear the floor with a mechanism and driving means of conventional design (not shown). A locking mechanism 65 holds foot rest 62 to table top 61 in any desired position along the tables length.

The x-ray source is mounted on a carriage which is not visible but is located within table body 60 and is adapted for being translated in opposite directions lengthwise of the patient. Extending upwardly from the carriage at the rear of the table is a column 66 which may be extended and contracted in a direction orthogonal to table top 61.

The improved spot film device is generally designated by reference numeral 67. It is supported on column 66 by means of a bearing support 68 that cooperates with a pair of bearing rails, such as the one marked 69, to enable the spot film device to be shifted manually to a limited extent crosswise of the table top forward to a locked examining position and locked toward a rear parked position.

Mounted to the top of spot film device 67 and near its front is a fluoroscopic device 70 including an x-ray image intensifier. A television camera, not shown, mounted within a housing 71 is used to display the x-ray image obtained during a fluoroscopic procedure on a television monitor, which is not shown but is well known to those who are skilled in the art.

A control panel 72 for operating the spot film device is located at its front end. Spot film device 67 has a front opening 73 for inserting and withdrawing a film cassette at the front of the table and a power assist handle 74 for controlling the position of the spot film device.

Figure 6:
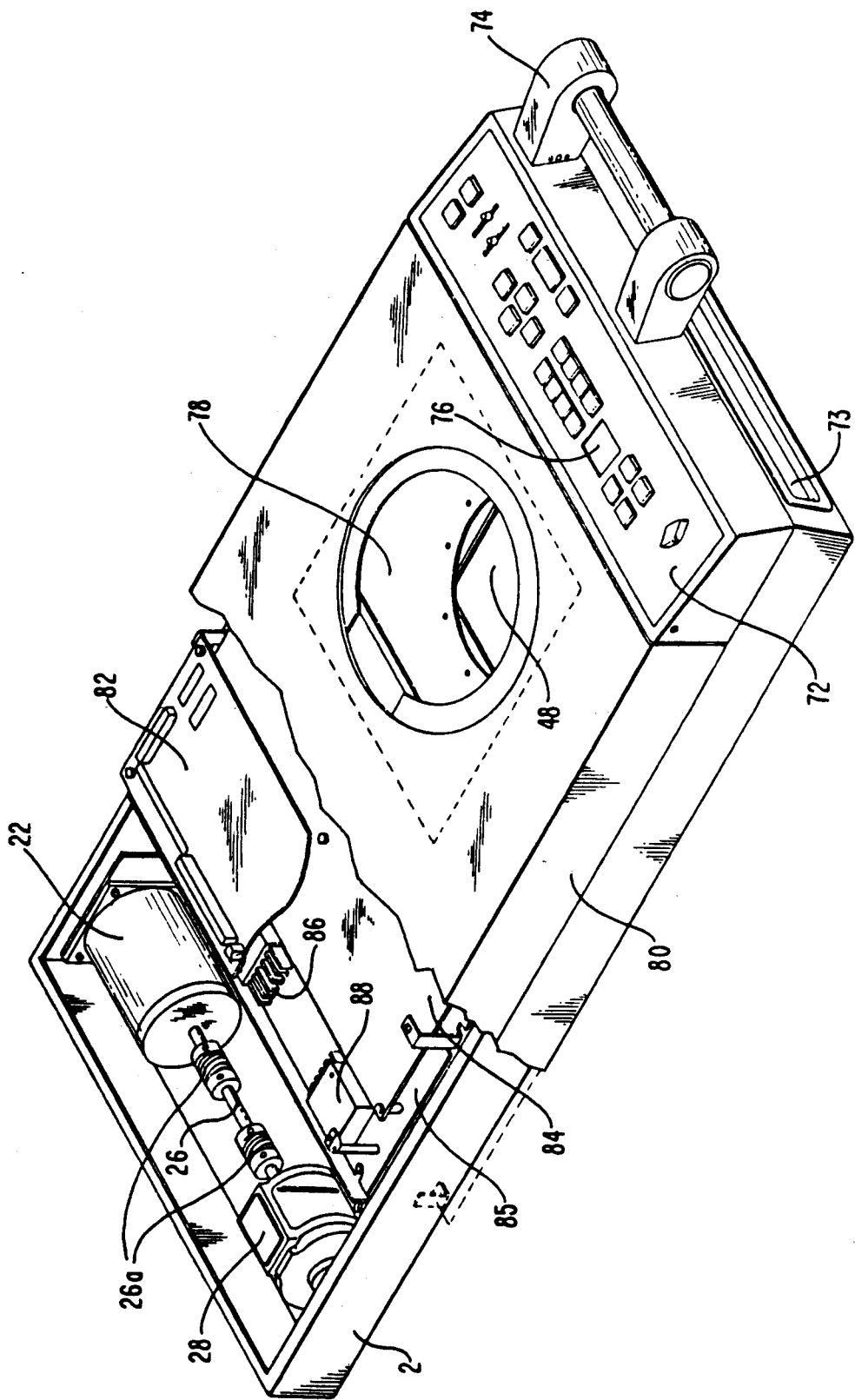
FIGS. 6, 7 and 8 illustrate an x-ray spot film device having a film cassette translation mechanism constructed in accordance with the principles of the present invention.
Figure 7:
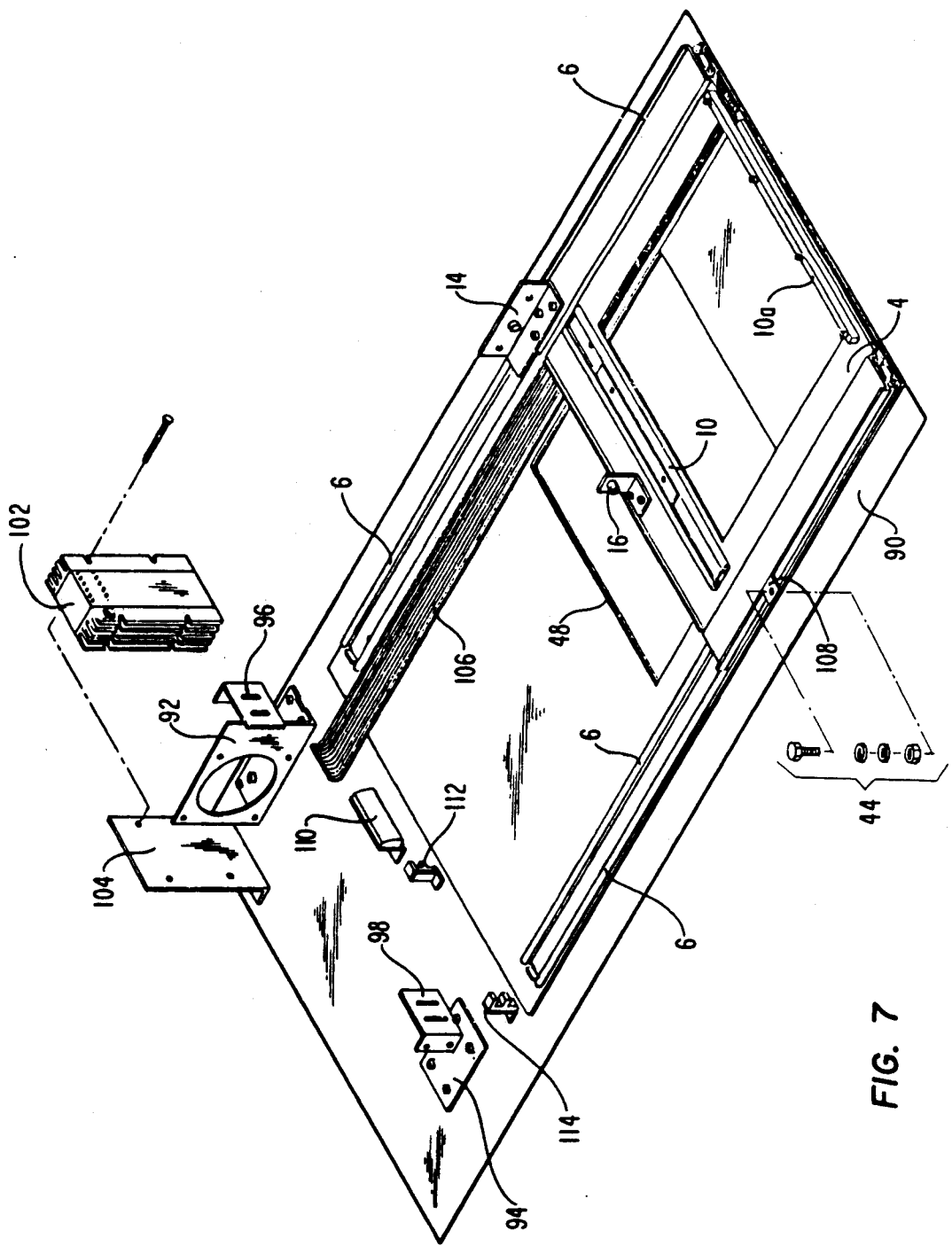
Figure 8:
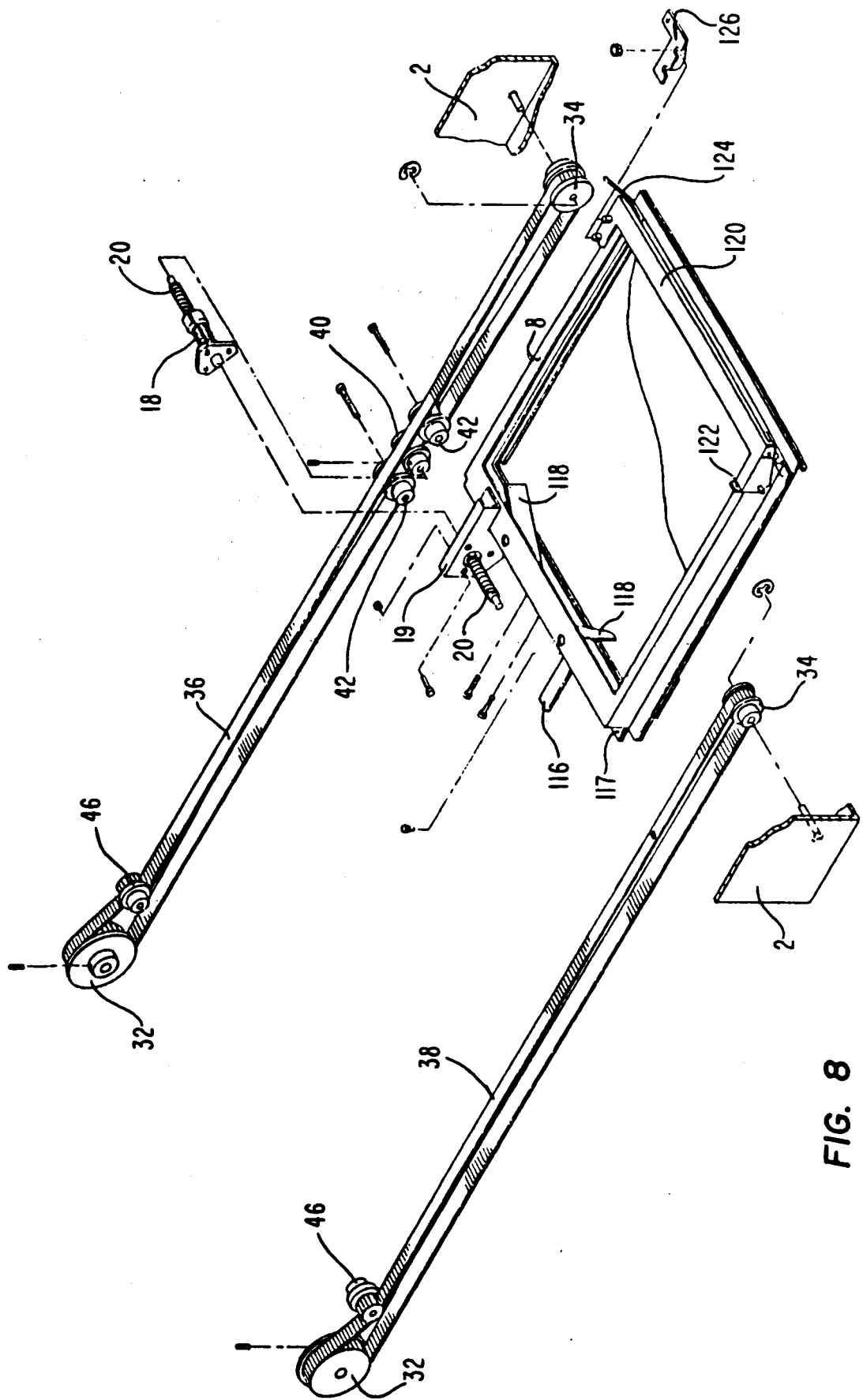

FIGS. 6, 7 and 8 illustrate details of the mechanical arrangement of the spot film device shown in FIG. 5. The reference numerals used in the preceding figures will be used herein for similarly functioning corresponding elements. In FIG. 6 the details of control panel 72 are shown as including a plurality of push-buttons for format selection, collimator control, table top position, table tilting, etc. A display 76 is also provided which comprises an array of LED's for displaying a graphic illustration of the format selection. X-ray port 48 is lead lined and includes a mounting arrangement 78 aligned therewith for the attachment of the fluoroscopic system above spot film device 67. In the rearward portion of spot film device 67, the cover 80 is shown cut-away so as to reveal the interior thereof. Thus, the position of motor 30 is shown as well as couplings 26a for coupling shaft 24 to clutch/brake assembly 28. Also shown are a circuit board 82 for mounting the relay/interface circuitry, a circuit board 84 mounted on a supporting platform 85 for the computer control circuitry and isolated and non-isolated power supplies 86 and 88, respectively. Motor 30 is a conventional four lead, four phase, 1.8° stepper motor driven by a 60 VDC, 6 amp, 20 kHz bi-polar chopper driver (module 102 shown in FIG. 7). Clutch/brake 28 is model CB-170 available from various well known electrical parts manufacturers, e.g., Electroid Corporation, etc.

FIG. 7 illustrates additional details relating to the mounting of components within frame 2. Thus, the bottom 90 of frame 2 is shown upon which mounting brackets 92 and 94 are provided for mounting motor 30 and clutch/brake assembly 28, respectively in their operating position. Additionally, brackets 6 and 98 are mounted on studs (mounted on the upper part of frame 2, not shown) for locating adjustable idler pulleys 46 (shown in FIG. 8). A motor drive module 102 is mounted on a bracket 104 and secured to bottom 90. An electrical ribbon cable 106 connects control panel 72 with interface circuit board 82 and passes underneath carriage 4. A side edge of carriage 4 includes a tab portion 108 having a hole therein for receiving screw arrangement 44 for clamping belt 38 to carriage 4. A rubber bumper 110 is provided to stop cassette 4 during rearward motion for a HOME position and optical sensors 112 and 114 are used to sense when holder 8 has returned to the HOME position (rear left corner).

FIG. 8 illustrates details of object holder 8 adapted to hold a film cassette. Holder 8 includes at its rearward portion a flag 116 and a lip 117 which cooperates with sensors 112 and 114, respectively, for indicating the y and x axis HOME position. A return spring 118 used for ejecting the film cassette when the holder latch 120 is raised. A tab 122 engages a spring latch mounted under control panel 72 for lifting holder latch 120 to allow the film cassette to be ejected. Holder latch 120 is returned to its closed position by a spring 124 attached to mount a 126. The remaining elements shown in FIG. 8 have already been described in conjunction with the prior figures.

Thus, there has been shown and described a novel dual axis translating mechanism which can rapidly position an object holder at any desired position along first and second axes in a simple, efficient and reliable manner. Many changes, modifications, variations and other uses and applications of the subject invention will, however, become apparent to those skilled in the art after considering this specification and its accompanying drawings, which disclose preferred embodiments thereof. For example, clutch/brake assembly 28 and coupling 26 could be replaced by a functional equivalent, such as a second independently controllable stepper motor which can be operated synchronously with motor 30 for obtaining the clutch (or drive) mode and energized so as to act as a brake for obtaining the brake mode. Of course, it should also be recognized that other types of motors could be used, such as a servo-motor. All such changes, modifications, variations and other uses and applications which do not depart from the spirit and scope of the invention are deemed to be covered by the invention which is limited only by the claims which follow.

What I claim is:

1. A mechanism for selective translation of an object along first and second axes, comprising:
   a frame;
   a carriage mounted on said frame so as to allow movement of said carriage with respect to said frame along a first axis;
   a holder for said object;
   intermediate mounting means coupled with said holder and said carriage for mounting said holder on said carriage so as to allow movement of said holder with respect to said carriage along a second axis which is different from said first axis;

a motor for selectively driving a first shaft;

a drive/brake assembly for providing a second shaft which, in a drive mode of said assembly is driven synchronously with said first shaft and, which in a brake mode of said assembly is held non-driven while said first shaft is being driven; and first and second endless belts mounted for rotating movement within said frame and extending in a direction parallel to said first axis, said first and second belts being coupled to said first and second shafts, respectively, for receiving selective rotational movement therefrom, with said first belt also being coupled to said intermediate mounting means for causing selective movement of said object holder in a direction parallel to said second axis during said brake mode of said drive/brake assembly and said second belt being coupled with said carriage for causing selective movement of said carriage in a direction parallel to said first axis and no movement of said object holder in a direction parallel to said second axis during said drive mode of said drive/brake assembly.

2. Apparatus according to claim 1, wherein said intermediate mounting means comprises:

a lead screw assembly fixedly mounted on said carriage and including a rotatable lead screw extending in a direction parallel to said second axis, said lead screw having a central portion rotatably coupled to said object holder and an end portion having a drive pulley thereon which is rotatably driven by said first endless belt.

3. Apparatus according to claim 2, wherein said object holder comprises:

a support arm extending therefrom which includes a nut for rotatably engaging the central portion of said lead screw for translating rotational movement of said lead screw into linear displacement of said object holder in a direction parallel to said second axis.

4. Apparatus according to claim 2, wherein:

said first endless belt is a notched belt, and first and second idler pulleys are coupled to said carriage for rotational movement adjacent opposite sides of said drive pulley for establishing a predetermined amount of wrap of said first endless belt around said drive pulley.

5. Apparatus according to claim 4, wherein:

said predetermined amount of wrap is greater than 100°.

6. Apparatus according to claim 1, wherein said intermediate mounting means comprises:

slide means mounted on said carriage and extending in a direction parallel to said second axis for engaging said object holder and effecting sliding movement thereof with respect to said carriage.

7. Apparatus according to claim 1, wherein said drive/brake assembly comprises:

a clutch/brake assembly having an input shaft which is driven by said first shaft via a coupling, and having an output shaft comprising said second shaft.

8. Apparatus according to claim 1, further including:

linear slide means mounted on said frame and extending parallel to said first axis for engaging said carriage and effecting sliding movement thereof with respect to said frame.

9. Apparatus according to claim 8, wherein said linear slide means comprises:

first and second ball bearing linear slides for engaging parallel sides of said carriage.

10. Apparatus according to claim 2, further including:

drive pulleys of the same size coupled to said first and second shafts for driving said first and second belts at equal linear speeds when said first and second shafts are being simultaneously driven.

11. Apparatus according to claim 1, wherein said mechanism for selective translation comprises a spot film device for a radiographic installation.

12. Apparatus according to claim 2, wherein said mechanism for selective translation comprises a spot film device for a radiographic installation.

13. A radiograph installation for providing fluoroscopic imaging and including a spot film device for selectively positioning an imaging object, said spot film device comprising:

a frame;

a carriage mounted on said frame so as to allow movement of said carriage with respect to said frame along a first axis;

a holder for said imaging object;

intermediate mounting means coupled with said holder and said carriage for mounting said holder on said carriage so as to allow movement of said holder with respect to said carriage along a second axis which is different from said first axis;

a motor for selectively driving a first shaft;

a clutch/brake assembly coupled to said motor for providing a second shaft which, in a clutch mode of said assembly is coupled with and driven by said first shaft and, which in a brake mode of said assembly is held non-driven while said first shaft is being driven; and first and second endless belts mounted for rotating movement within said frame and extending in a direction parallel to said first axis, said first and second belts being coupled to said first and second shafts, respectively, for receiving selective rotational movement therefrom, with said first belt also being coupled to said intermediate mounting means for causing selective movement of said object holder in a direction parallel to said second axis and said second belt being coupled with said carriage for causing selective movement of said carriage in a direction parallel to said first axis.

14. Apparatus according to claim 13, further including:

drive pulleys of the same size coupled to said first and second shafts for driving said first and second belts at equal linear speeds when said first and second shafts are being simultaneously driven, so that during said clutch mode of said clutch/brake assembly said first and second belts simultaneously receive the same selective rotational movement from said first and second shafts, respectively, for causing movement of said carriage in a direction parallel to said first axis and no movement of said object holder in a direction parallel to said second axis.

15. Apparatus according to claim 13, wherein said intermediate mounting means comprises:

a lead screw assembly fixedly mounted on said carriage and including a rotatable lead screw extending in a direction parallel to said second axis, said lead screw having a central portion rotatably coupled to said object holder and an end portion having a drive pulley thereon which is rotatably driven by said first endless belt.

16. Apparatus according to claim 15, wherein said object holder comprises:
a support arm extending therefrom which includes a nut for rotatably engaging the central portion of said lead screw for translating rotational movement of said lead screw into linear displacement of said object holder in a direction parallel to said second axis.

17. Apparatus according to claim 15, wherein:
said first endless belt is a notched belt, and first and second idler pulleys are coupled to said carriage for rotational movement adjacent opposite sides of said drive pulley for establishing a predetermined amount of wrap of said first endless belt around said drive pulley.

18. Apparatus according to claim 17, wherein:
said predetermined amount of wrap is greater than 100°.

19. Apparatus according to claim 13, wherein said intermediate mounting means comprises:
slide means mounted on said carriage and extending in a direction parallel to said second axis for engaging said object holder and effecting sliding movement thereof with respect to said carriage.

20. Apparatus according to claim 15, further including:
drive pulleys of the same size coupled to said first and second shafts for driving said first and second belts at equal linear speeds when said first and second shafts are being simultaneously driven.

21. Apparatus according to claim 13, wherein said linear slide means comprises:
first and second ball bearing linear slides for engaging parallel sides of said carriage.

22. A mechanism for selective translation of an object along first and second axes, comprising:
a frame;
a carriage mounted on said frame so as to allow movement of said carriage with respect to said frame along a first axis;
a holder for said object;
a lead screw assembly coupled with said holder and said carriage for mounting said holder on said carriage so as to allow movement of said holder with respect to said carriage along a second axis which is different from said first axis, said lead screw assembly including a rotatable lead screw extending in a direction parallel to said second axis and having a central portion rotatably coupled to said object holder and an end portion having a drive pulley thereon;
a motor for selectively driving a first shaft;
a drive/brake assembly for providing a second shaft which, in a drive mode of said assembly is driven synchronously with said first shaft and, which in a brake mode of said assembly is held non-driven while said first shaft is being driven; and
first and second endless belts mounted for rotating movement within said frame and extending in a direction parallel to said first axis, said first and second belts being coupled to said first and second shafts, respectively, for receiving selective rotational movement therefrom, with said first belt also being coupled to said lead screw drive pulley for rotating said lead screw and thereby causing selective movement of said object holder in a direction parallel to said second axis, and said second belt also being coupled with said carriage for causing selective movement of said carriage in a direction parallel to said first axis.

23. Apparatus according to claim 22, wherein said object holder comprises:
a support arm extending therefrom which includes a nut for rotatably engaging the central portion of said lead screw for translating rotational movement of said lead screw into linear displacement of said object holder in a direction parallel to said second axis.

24. Apparatus according to claim 22, wherein said mechanism for selective translation comprises a spot film device for a radiographic installation.

25. Apparatus according to claim 24, wherein said mechanism for selective translation comprises a spot film device for a radiographic installation.

* * * * *